US010918522B2

(12) United States Patent
Bacher et al.

(10) Patent No.: US 10,918,522 B2
(45) Date of Patent: Feb. 16, 2021

(54) PHOTODISRUPTION-BASED VITRECTOMY SYSTEM

(71) Applicant: NOVARTIS AG, Basel (CH)

(72) Inventors: Gerald David Bacher, Carlsbad, CA (US); Brian William McDonell, Irvine, CA (US); Michael J. Papac, North Tustin, CA (US)

(73) Assignee: Alcon Inc., Fribourg (CH)

( * ) Notice: Subject to any disclaimer, the term of this patent is extended or adjusted under 35 U.S.C. 154(b) by 4 days.

(21) Appl. No.: 16/002,465

(22) Filed: Jun. 7, 2018

(65) Prior Publication Data
US 2018/0353328 A1 Dec. 13, 2018

Related U.S. Application Data

(60) Provisional application No. 62/516,744, filed on Jun. 8, 2017.

(51) Int. Cl.
*A61F 9/00* (2006.01)
*A61F 9/008* (2006.01)
(Continued)

(52) U.S. Cl.
CPC .......... *A61F 9/0084* (2013.01); *G02B 6/3518* (2013.01); *A61F 2009/00874* (2013.01);
(Continued)

(58) Field of Classification Search
CPC ......... A61F 9/0084; A61F 2009/00874; G02B 6/3518; G02B 6/02042; G02B 6/02328; G02B 6/3512; G02B 6/3598
See application file for complete search history.

(56) References Cited

U.S. PATENT DOCUMENTS 5,112,328 A 5/1992 Taboada et al.
5,123,902 A 6/1992 Mueller
(Continued)

FOREIGN PATENT DOCUMENTS

CA 2754744 A1 9/2010
WO WO2013085736 A1 6/2013
WO WO2017023296 A1 2/2017

OTHER PUBLICATIONS

Boyle, Erin L., EyeWorld News Service, "Femtosecond laser offers potential for additional indications", Ophthalmology Magazine, Sep. 2013, pp. 1-8.
(Continued)

*Primary Examiner* — Christopher Koharski
*Assistant Examiner* — Roland Dinga (57) ABSTRACT

In a general aspect, a vitrectomy system is adapted to use photodisruption to rupture eye tissue. In some aspects, a photodisruption-based vitrectomy system includes a laser source configured to generate optical pulses having a pulse energy greater than a threshold energy for causing photodisruption in vitreous humor. The system also includes an optical switching device arranged to receive an output of the laser source, and an optical fiber with multiple cores that is arranged to receive an output of the optical switching device. The optical switching device is configured to select a core of the optical fiber and direct optical pulses received from the laser source into the selected core.

20 Claims, 5 Drawing Sheets

(51) Int. Cl.
*G02B 6/35* (2006.01)
*G02B 6/02* (2006.01)

(52) U.S. Cl.
CPC ...... *G02B 6/02042* (2013.01); *G02B 6/02328* (2013.01); *G02B 6/3512* (2013.01); *G02B 6/3598* (2013.01)

(56) References Cited

U.S. PATENT DOCUMENTS

| | | |
|---|---|---|
| 5,246,436 A | 9/1993 | Rowe |
| 5,738,677 A | 4/1998 | Colvard |
| 6,066,128 A | 5/2000 | Bahmanyar et al. |
| 8,398,240 B2 | 3/2013 | Smith |
| 8,480,233 B2 | 7/2013 | Smith |
| 8,764,736 B2 | 7/2014 | Kurtz |
| 8,837,883 B2 | 9/2014 | Lassalas |
| 8,900,139 B2 | 12/2014 | Yadlowsky |
| 8,903,476 B2 | 12/2014 | Brennan et al. |
| 9,055,885 B2 | 6/2015 | Horvath |
| 9,456,925 B2 | 10/2016 | Kurtz |
| 9,579,153 B2 | 2/2017 | Dick et al. |
| 9,615,969 B2 | 4/2017 | Nissan |
| 9,730,576 B2 | 8/2017 | Yadlowsky |
| 9,956,053 B2 | 5/2018 | Diao |
| 10,039,669 B2 | 8/2018 | Heeren |
| 10,238,543 B2 | 3/2019 | Farley |
| 10,292,783 B2 | 5/2019 | Bacher |
| 10,307,290 B2 | 6/2019 | Kern |
| 10,478,266 B2 | 11/2019 | Mirsepassi |
| 2003/0133186 A1* | 7/2003 | Reznichenko ....... G02B 6/3582 359/366 |
| 2004/0109634 A1* | 6/2004 | Basavanhally ...... G02B 6/3582 385/18 |
| 2010/0318074 A1 | 12/2010 | Daquay |
| 2016/0120699 A1* | 5/2016 | Farley .................. A61F 9/0084 606/4 |
| 2016/0174812 A1 | 6/2016 | Artsyukhovich |
| 2017/0100285 A1 | 4/2017 | Hallen |
| 2017/0172802 A1 | 6/2017 | Papac |
| 2017/0333252 A1 | 11/2017 | Biancalana |
| 2018/0132963 A1 | 5/2018 | Diao |
| 2018/0133057 A1 | 5/2018 | Diao |
| 2018/0168861 A1 | 6/2018 | Mirsepassi |
| 2018/0338776 A1 | 11/2018 | Farley |
| 2018/0360660 A1 | 12/2018 | Lopez |
| 2019/0175407 A1 | 6/2019 | Bacher |
| 2019/0201238 A1 | 7/2019 | Bacher |
| 2019/0209372 A1 | 7/2019 | Farley |
| 2019/0298571 A1 | 10/2019 | Mcdonell |
| 2019/0388274 A1 | 12/2019 | Claus |

OTHER PUBLICATIONS

RP Photonics Encyclopedia, "Hollow-core Fibers", Encyclopedia of Laser Physical and Technology; https://www.rp-photonics.com/hollow_core_fibers.

Saitoh, K. and Matsuo, S., Multicore Fiber Technology, Journal of Lightwave Technology, vol. 34, No. 1, pp. 55-56, Jan. 1, 2016.

* cited by examiner

PHOTODISRUPTION-BASED VITRECTOMY SYSTEM

BACKGROUND

The following description relates to a photodisruption-based vitrectomy system.

Certain ophthalmic surgical procedures require the removal of eye tissue. For instance, a needle of a handpiece of a vitrectomy system may be inserted into the eye to remove vitreous humor during a surgical procedure. Typical vitrectomy systems utilize small, complex mechanical means to cut the vitreous humor within the needle.

Photodisruption is a phenomenon that occurs in tissue when high energy optical pulses cause vapor bubbles to form in the tissue, resulting in a rupture of the tissue. Photodisruption has been used in certain ophthalmic procedures, such as, for example, to cut flaps in the cornea and for dissection of the lens in cataract surgery.

SUMMARY

In a general aspect, a vitrectomy system causes photodisruption in vitreous humor of an eye.

In some aspects, a photodisruption-based vitrectomy system includes a laser source configured to generate optical pulses having a pulse energy greater than a threshold energy for causing photodisruption in vitreous humor. The system also includes an optical switching device arranged to receive an output of the laser source, and an optical fiber with multiple cores that is arranged to receive an output of the optical switching device. The optical switching device is configured to select a core of the optical fiber and direct optical pulses received from the laser source into the selected core.

In some aspects, a method for operating a photodisruption-based vitrectomy system includes directing an optical pulse generated by a laser source toward an optical switching device and selecting, by the optical switching device, a core of a multi-core optical fiber. The method also includes directing, by the optical switching device, the optical pulse into the selected core of the optical fiber. The optical pulses have an energy greater than a threshold energy for causing photodisruption in vitreous humor.

In some aspects, an ophthalmic surgical system includes a console and a handpiece coupled to the console. The console includes a laser source configured to generate optical pulses having a pulse energy greater than a threshold energy for causing photodisruption in vitreous humor, and an optical switching device in optical communication with the laser source. The handpiece includes a body and a needle extending from the body. The needle defines an opening, and an optical fiber with multiple cores is disposed within the needle. An end of the optical fiber is disposed proximate to the opening in the needle. The optical switching device is configured to select a core of the multi-core optical fiber and direct optical pulses from the laser source into the selected core.

The details of one or more implementations are set forth in the accompanying drawings and the description below. Other features, objects, and advantages will be apparent from the description and drawings, and from the claims.

DETAILED DESCRIPTION

In some aspects of what is described here, a vitrectomy system is adapted to use photodisruption to rupture eye tissue. Photodisruption may refer to the rupture of tissue caused by an optical pulse that interacts with the eye tissue. The optical pulse may cause an increase in the temperature of the tissue, forming plasma vapor bubbles in the tissue which then rupture. In some aspects, for example, a handpiece of a vitrectomy system includes a needle with an optical fiber disposed therein, and optical pulses are directed down the optical fiber when the needle is inserted into the eye. The optical pulses have characteristics such that, upon exiting the optical fiber, the pulses have an energy (e.g., intensity) that is sufficient to cause photodisruption in tissue of the eye (e.g., vitreous humor). To ensure that the optical pulses have enough intensity to cause photodisruption in the tissue, in some instances, the beam exiting the optical fiber may be focused to a small beam width (e.g., approximately 1 to 50 micrometers ($\mu$m) in diameter), which may depend on the pulse energy of the optical pulses.

In some aspects, the optical fiber in the handpiece of the vitrectomy system includes multiple cores, and the vitrectomy system includes an optical switching device that selects a core of the optical fiber into which to direct each optical pulse. The cores of the multi-core fiber may be arranged in one- or two-dimensional patterns across the cross-sectional area of the optical fiber to allow for a wider area over which photodisruption may occur compared to a vitrectomy system with a single-core optical fiber. For example, in some instances, optical pulses may be directed into some or all of the cores in the optical fiber to increase an area over which photodisruption occurs in the eye tissue.

In some aspects, the pulse energy of the optical pulses may be varied such that photodisruption occurs at different distances away from the optical fiber (based on the pulse energy). Because photodisruption is a threshold-based process, the photodisruption will begin and continue until the intensity of the optical pulses fall below a threshold. By increasing the pulse energy, the point at which photodisruption occurs after exiting the optical fiber will be closer to the exit of the optical fiber. Accordingly, by controlling the energy of the optical pulses directed toward the optical fiber, the distance from the optical fiber at which photodisruption occurs may be controlled. Varying the energy of the optical pulses may therefore increase a depth over which photodisruption occurs.

Aspects of what is described here may provide certain advantages. In some aspects, for example, eye tissue (e.g., vitreous humor) may be removed during an ophthalmic surgical procedure using photodisruption rather than mechanical means. In addition, the area of photodisruption occurring within a needle of a vitrectomy system may be enlarged by "scanning" the cores of a multi-core optical fiber (e.g., directing optical pulses down different cores of the optical fiber). Furthermore, the depth over which photodisruption occurs within the needle may be enlarged by varying the pulse energy of the optical pulses. In some instances, the volume over which photodisruption occurs may be enlarged by scanning the cores of the multi-core optical fiber and varying the energy of the optical pulses. The area or volume may be enlarged without the need for any mechanical apparatus inside the small volume of the needle of the handpiece.

Figure 1:
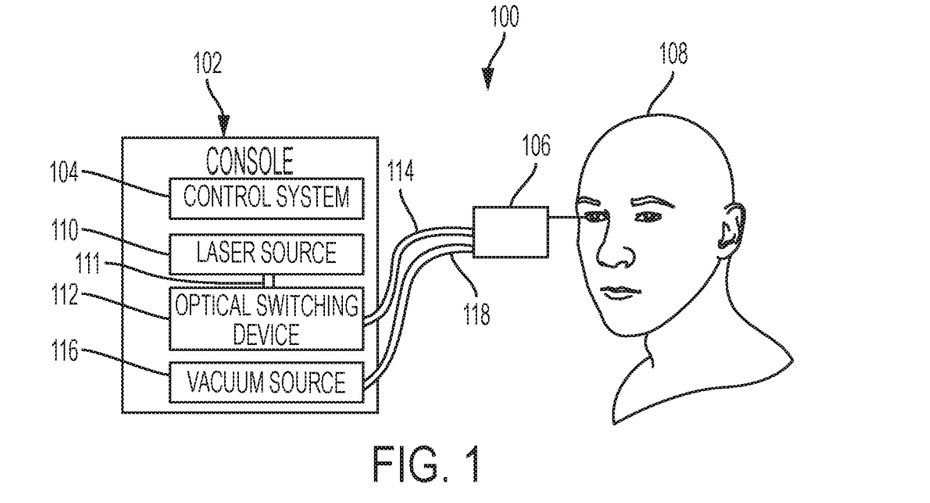
FIG. 1 is a diagram showing an example photodisruption-based vitrectomy system performing an ophthalmic surgical procedure.

FIG. 1 is a diagram showing an example photodisruption-based vitrectomy system 100 performing an ophthalmic surgical procedure. The example system 100 includes a console 102 with a control system 104, a laser source 110, an optical switching device 112, and a vacuum source 116. In the example shown, the laser source 110 is in optical communication with the optical switching device 112 though the optical fiber 111, and the optical switching device 112 is in optical communication with the handpiece 106 through the optical fiber 116. Furthermore, in the example shown, the vacuum source 116 is in fluid communication with the handpiece 106 through cable 118. In some implementations, the optical switching device 112 may be disposed in another location, such as, for example, inside the handpiece 106.

Figure 2:
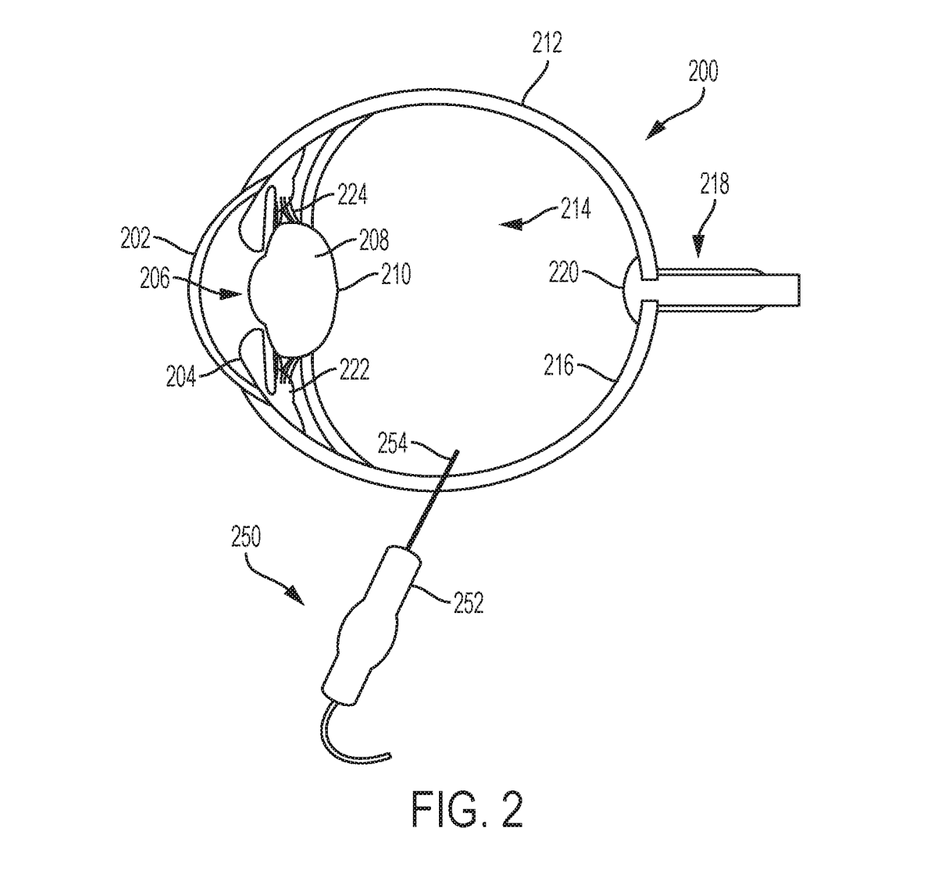
FIG. 2 is a diagram showing an example handpiece of a photodisruption-based vitrectomy system inserted into vitreous humor of an eye.

In some implementations, the example handpiece 106 is used by an operator (e.g., a surgeon) during a surgical procedure relating to the eye. For example, the handpiece 106 may be used to remove vitreous humor from the eye of the patient 108 by causing photodisruption in the vitreous humor or other tissues of the eye. A needle of the handpiece 106 may be inserted into the eye of a patient 108 during such a procedure, as shown in FIGS. 1 and 2, to rupture the eye tissue using photodisruption and remove the eye tissue.

In some implementations, the example optical fiber 114 is a multi-core optical fiber. The optical fiber 114 may run from the console 102 to the handpiece 106 as shown in FIG. 1, and may further run through a needle extending from the body of the handpiece 106 (similar to the optical fiber 312 disposed within the needle 304 of the handpiece 300 of FIG. 3). The example optical switching device 112 may be configured to select a core of the optical fiber 114 and direct pulses generated by the laser source 110 into the selected core. The optical switching device 112 may include any suitable device for selectively directing optical pulses into the optical fiber. For example, in some instances, the optical switching device 112 includes a microelectromechanical system (MEMS) device or a mirror galvanometer. The optical fiber 114 may be any suitable waveguide for directing optical signals in multiple cores. For example, in some implementations, the optical fiber is a glass fiber with multiple glass cores. In some implementations, the optical fiber is a hollow-core optical fiber with multiple gas cores, such as, for example, a photonic crystal fiber or photonic bandgap fiber. The optical switching device 112 may selectively direct optical pulses generated by the laser source 110 into the cores of the optical fiber 114. The optical pulses generated by the laser source 110 have enough energy to cause photodisruption in eye tissue (e.g., vitreous humor) when exiting the optical fiber 114 in the needle of the handpiece 106.

The example console 102 includes components that control and operate one or more components of the ophthalmic surgical system 100. For instance, in the example shown, the console 102 includes a laser control system 104 that provides signals to the laser source 110 and/or the optical switching device 112. The control system 104 may include a processor, a memory, software, and firmware that are configured to control aspects of the laser source 110 and the optical switching device 112. For example, in some implementations, the control system 104 is configured to provide signals to the optical switching device 112 that cause the optical switching device 112 to direct optical pulses generated by the laser source 110 into selected cores of the multi-core optical fiber 114. In some implementations, the control system 104 is configured to provide signals to the laser source 110 that control (e.g., increase, decrease, or otherwise vary) the pulse energy, pulse rate, pulse length, etc. of optical pulses generated by the laser source 110 and sent to the optical switching device 112.

The example laser source 110 generates optical pulses having one or more characteristics that allow for effective photodisruption in eye tissue, such as vitreous humor. For example, the laser source 110 may include a femtosecond laser oscillator, such as a Ytterbium-based (e.g., a Yb:Glass or Yb-doped fiber) laser, an Erbium-based (e.g., an Er-doped fiber) laser, a Titanium Sapphire ($TiAl_2O_3$) laser, Chromium-based (e.g., Cr:LiSAF Cr:LiCAF, or Cr:LiSGAF) laser, an Alexandrite laser, a neodymium-doped yttrium aluminum garnet (Nd:YAG) laser, a semiconductor- or dye-based laser, or another type of laser. The laser source 110 may generate optical pulses having a pulse energy greater than a threshold energy for causing photodisruption in vitreous humor. For example, the laser source 110 may generate pulses having a pulse energy between approximately 1 microjoule (µJ) to 10 millijoules (mJ), and a temporal width between approximately 10-1000 femtoseconds (fs). In some instances, the laser source 110 may be a 10 MW peak power laser that produces optical pulses having a pulse energy of approximately 5 mJ. The laser source 110 may generate optical pulses at a rate between approximately 10-500 kilohertz (kHz). In some instances, for example, the laser source 110 may generate optical pulses having a pulse energy of 1 millijoules (mJ) and a temporal width of 500 femtoseconds (fs) at a rate of 100 kilohertz (kHz). The optical fiber 111 may include fiber optic cable that is designed to effectively propagate the optical pulses generated by the laser source 110 to the optical switching device 112.

The example vacuum source 116 is used to remove eye tissue (e.g., vitreous humor) from the eye of the patient 108 during an ophthalmic surgical procedure, such as a vitrectomy. For example, the vacuum source 116 may be in fluid communication with an aspiration lumen inside the handpiece 106 through cable 118. The vacuum source 116 may provide a vacuum pressure to the aspiration lumen that forces the eye tissue in a needle of the handpiece 106 to be removed and sent to the console 102 through the cable 118.

FIG. 2 is a diagram showing an example handpiece 250 of a photodisruption-based vitrectomy system inserted into vitreous humor 214 of an eye 200. The eye 200 includes a cornea 202, an iris 204, a pupil 206, a lens 208, a lens capsule 210, zonules 224, a ciliary body 222, a sclera 212, vitreous humor 214, a retina 216, a macula 220, and an optic nerve 218. The cornea 202 is a clear, dome-shaped structure on the surface of the eye that acts as a window, letting light into the eye 200. The iris 204 is the colored part of the eye 200, a muscle surrounding the pupil 206 that relaxes and contracts to control the amount of light entering the eye 200. The pupil 206 is the round, central opening of the iris 204. The lens 208 is a structure inside the eye 200 that primarily helps to focus light on the retina 216. The lens capsule 210 is an elastic bag that envelops and helps to control the shape of the lens 208 when the eye 200 focuses on objects at different distances. The zonules 224 are slender ligaments that attach the lens capsule 210 to the inside of the eye 200, holding the lens 208 in place. The ciliary body 222 is the muscular area attached to the lens 208 that contracts and relaxes to control the size of the lens 208 for focusing of the eye 200. The sclera 112 is the tough, outermost layer of the eye 200 that maintains the shape of the eye 200. The vitreous humor 214 fills the large section of the eye 200 that is located towards the back of the eyeball and helps to maintain the curvature of the eye 200. The retina 116 is a light-sensitive nerve layer in the back of the eye 200 that receives light and converts it into signals to send to the brain. The macula 120 is the area in the back of the eye 200 that contains functions for seeing fine detail. The optic nerve 118 connects and transmits signals from the eye 200 to the brain.

The example handpiece 250 includes a body 252 and a needle 254. As shown in FIG. 2, the needle 254 of the handpiece 250 may be inserted into the eye 200 to remove portions of the vitreous humor 214. The body 252 may be used by an operator of the handpiece 250 to control the location of the needle 254 during operation. During operation, the needle 254 of the handpiece 250 may be placed nearby an area of the eye 200 in which the operator wishes to remove vitreous humor 214. To remove the vitreous humor 214, an optical fiber within the needle 254 (e.g., similar to the optical fiber 312 inside the needle 304 of the handpiece 300 of FIG. 3) directs optical pulses toward the vitreous humor 214 within the needle 254. The optical pulses have enough energy (e.g., intensity) to cause photodisruption in the vitreous humor after exiting the optical fiber. In some instances, the optical pulses have a pulse energy between 1 microjoule (μJ) to 10 millijoules (mJ), and a temporal width between 10-1000 femtoseconds (fs). In some implementations, the optical fiber in the needle 254 is a multi-core optical fiber and an optical switching device (e.g., similar to the optical switching device 112 of FIG. 1 located in a remote console, or an optical switching device located in the handpiece 250) selects a core of the multi-core optical fiber and direct pulses from a laser source into the selected core. For example, the handpiece 250 may include one or more of the components illustrated in FIGS. 3 and 4A-4D and described below.

Figure 3:
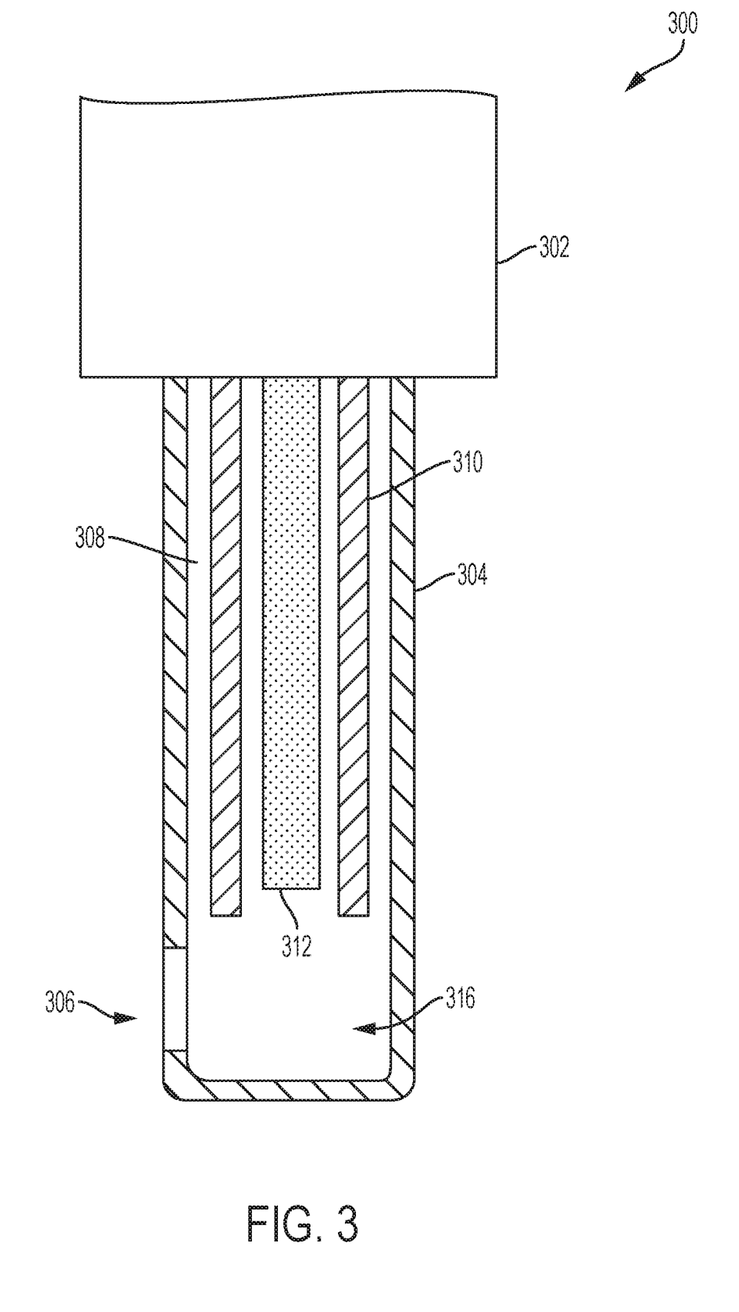
FIG. 3 is a diagram showing a side view of an example handpiece of a photodisruption-based vitrectomy system.

FIG. 3 is a diagram showing a side view of an example handpiece 300 of a photodisruption-based vitrectomy system. The handpiece 300 may be used to remove vitreous humor from an eye, similar to the handpiece 106 of FIG. 1 or the handpiece 250 of FIG. 2. The example handpiece 300 includes a body 302 and a needle 304. In some implementations, the body 302 forms a handle portion that may be grasped and manipulated by an operator (e.g., a surgeon) when performing an ophthalmic surgical procedure. The body 302 may be composed of any suitable material, such as, for example, lightweight aluminum, a polymer, or another material.

The needle 304 is coupled to, and extends from, the body 302. In some implementations, the needle 304 is designed to penetrate a globe of an eye to remove vitreous humor from the eye (as shown in FIG. 2). The needle 304 defines an opening 306 that is sized to allow tissue (e.g., vitreous humor) to enter the interior of the needle. In the example shown, a first end of the needle 304 is coupled to the body 302 and the opening 306 is defined proximate to a second, opposite end of the needle 304. The needle 304 may define the opening 306 in another location, or may define multiple openings. In some implementations, the opening 306 is circular with a diameter of approximately three hundred (300) micrometers (μm). The needle 304 also includes an aspiration lumen 308 that is sized to allow fluid flow between the opening 306 and the body 302 of the handpiece 300.

The example handpiece 300 includes a multi-core optical fiber 312 disposed within the needle 304. The multi-core optical fiber 312 comprises multiple cores through which optical signals may travel. In the example shown, the multi-core optical fiber 312 is disposed within a cannula 310 inside the needle 304. The cannula 310 defines an aspiration lumen 308 within the needle 304. In the example shown, the aspiration lumen 308 has an annular shape. The aspiration lumen 308 may be sized to allow for the aspiration of ruptured vitreous humor from the eye after photodisruption has occurred (e.g., sized to allow the rupture vitreous humor fluid to flow from the opening 306 or area 316 into the body 302 and elsewhere).

The multi-core optical fiber 312 is positioned such that optical signals (e.g., femtosecond optical pulses) travelling in and projecting from the optical fiber 312 will be projected across the opening 306 in the area 316. For example, the end of the multi-core optical fiber 312 may be disposed proximate to the opening 306, as shown in FIG. 3. In some implementations, the multi-core optical fiber 312 terminates with a rounded tip that operates as a lens. The rounded tip may concentrate the energy of the optical signals exiting the fiber by reducing the divergence of the beam, collimating the beam, or focusing the beam to a spot smaller than the optical fiber diameter. For example, in some implementations, the rounded tip may focus a beam projected from the optical fiber 312 to a circular spot with a diameter of approximately ten (10) to twenty-five (25) micrometers (μm). The size of the spot may depend on the energy of the beam. For example, larger energy beams may be focused into larger spots to avoid beam intensities that are too high (since high intensity beams may cause unwanted effects). Conversely, lower energy beams may be focused into smaller spots to ensure the beam has an intensity that is high enough to cause photodisruption in the eye tissue.

In some instances, this spot may be the effective area over which photodisruption occurs in the area 316. However, by selectively directing optical signals down each of the cores of the multi-core optical fiber 312, the effective area over which photodisruption occurs in the area 316 may be enlarged. Furthermore, because photodisruption is a threshold process as described above, by varying the energy of the optical pulses travelling in and projecting from the optical fiber 312, the location of the spot over which photodisruption occurs in the area 316 may be moved.

Figure 4A:
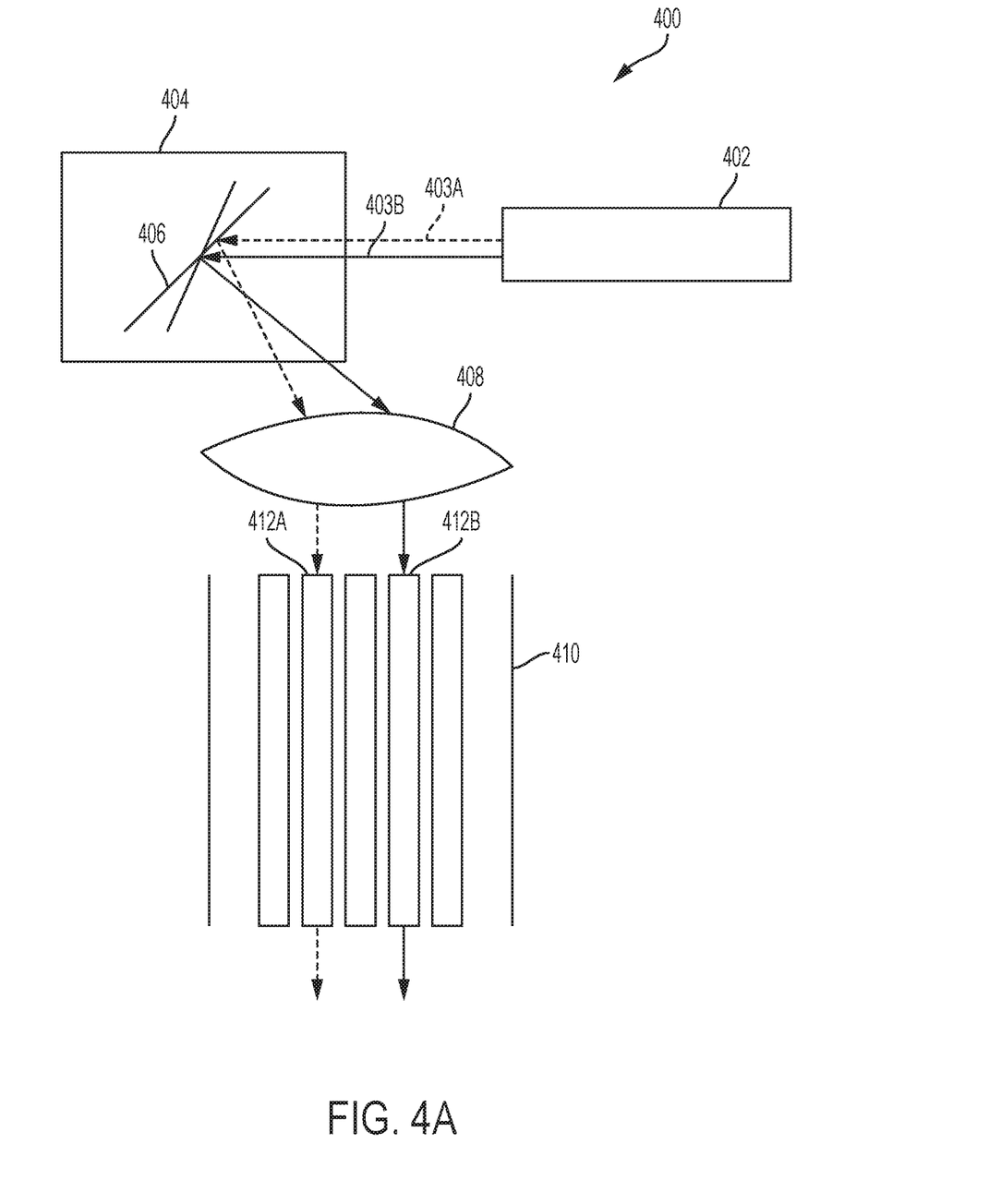
FIGS. 4A-4D are diagrams showing aspects of operation of an example photodisruption-based vitrectomy system.

FIGS. 4A-4D are diagrams showing aspects of operation of an example photodisruption-based vitrectomy system 400. FIG. 4A illustrates aspects of the selection of cores of a multi-core optical fiber 410 by an optical switching device 404. In the example shown in FIG. 4A, the photodisruption system 400 includes a laser source 402, an optical switching device 404, and an optical fiber 410 that includes multiple cores 412. The laser source 402 may include a femtosecond or picosecond laser oscillator, and may be configured to generate optical pulses having a peak energy between 1 microjoule (μJ) to 10 millijoules (mJ) and a temporal width between 10-1000 femtoseconds (fs). In some instances, the laser source 402 includes a Ytterbium-based (e.g., a Yb:Glass or Yb-doped fiber) laser, an Erbium-based (e.g., an Er-doped fiber) laser, a Titanium Sapphire (TiAl$_2$O$_3$) laser, Chromium-based (e.g., Cr:LiSAF Cr:LiCAF, or Cr:LiSGAF) laser, an Alexandrite laser, or a neodymium-doped yttrium aluminum garnet (Nd:YAG) laser. In some instances, the laser source 402 includes a chirped pulse laser amplification system coupled to a laser oscillator. The laser source 402 may have a pulse repetition rate between approximately 10-500 kilohertz (kHz).

The laser source 402 generates beams 403 of optical pulses that are directed toward the optical switching device 404. The beams 403 may include one or more optical pulses, in some instances. The optical switching device 404 may be implemented with one or more mirrors that selectively direct optical pulses from the laser source 402 into particular cores 412 of the multi-core optical fiber 410. In some implementations, the optical switching device 404 is a microelectromechanical system (MEMS) device. In some implementations, the optical switching device 404 is a mirror galvanometer. The optical switching device 404 is configured to direct beams from the laser source 402 toward any core 412 of the optical fiber 410. In the example shown, for instance, the laser source 402 generates a first beam 403A that is directed toward the core 412A by the mirror 406, and a second beam 403B that is directed toward the core 412B by the mirror 406. The beams 403 may be directed into the cores 412 by way of a lens 408 that is disposed in an optical path between the optical switching device 404 and the optical fiber 410, as shown. Although shown in FIG. 4A as being separate from the optical switching device 404, the lens 408 may be disposed within the optical switching device (e.g., both the mirrors 406 and the lens 408 may be disposed within the same unit, e.g., in an optical switching device disposed within a console of a vitrectomy system, such as optical switching device 112 of FIG. 1, or within a handpiece of a vitrectomy system).

The optical switching device 404 may select the cores 412 in any suitable order. For example, the optical switching device 404 may select the cores 412 of the optical fiber 410 sequentially (e.g., in a raster-scan manner) into each respective core of the optical fiber. The optical switching device 404 may also select the cores 412 based on another pattern, randomly, or in any other another manner. For example, the optical switching device 404 may select cores 412 according to a pattern that avoids selecting adjacent cores consecutively. By selectively directing the beams 403 optical pulses into the various cores 412, the area over which photodisruption occurs may be increased. In some implementations, the optical switching device 404 selects and directs optical pulses from the laser source 402 based on a pulse rate of the laser source 402. For example, the optical switching device 404 may select a new core 412 to direct optical pulses into after 1, 2, 5, 10, 100, or another number of pulses generated by the laser source 402. For instance, if the laser source 402 has a pulse rate of 100 kHz, then the optical switching device 404 may select a new core to direct pulses into at a rate of 100 kHz, 50 kHz, 20 kHz, 10 kHz, or 1 kHz, respectively.

Figure 4B:
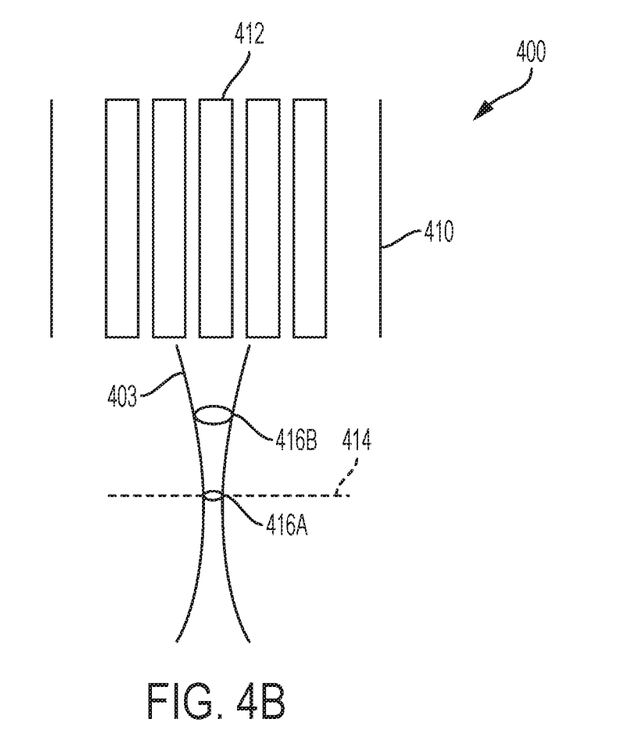

FIG. 4B illustrates aspects of varying a pulse energy of optical pulses generated by the laser source 402. In the example shown in FIG. 4B, as the beam 403 exits the core 412 it is focused toward a focal point at a particular focal distance 414 away from the end of the optical fiber 412. The beam 403 converges into a spot 416A at the focal distance 414. In some instances, the optical pulses in the beam 403 have characteristics (e.g., a particular intensity) that allow the beam 403 to cause photodisruption in eye tissue at the spot 416A. Because the photodisruption process is a threshold process, when the pulse energy of the optical pulses is increased, the beam 403 may cause photodisruption in eye tissue at a shorter distance from the end of the optical fiber 410 than the focal distance 414. For example, optical pulses with increased pulse energy may cause photodisruption at the spot 416B rather than at spot 416A. By varying the energy of the optical pulses generated by the laser source 402, the location at which photodisruption occurs may be controlled. Such techniques may be used in conjunction with those described above with respect to FIG. 4A to allow for a larger volume over which photodisruption occurs in a photodisruption-based vitrectomy system.

Figure 4C:
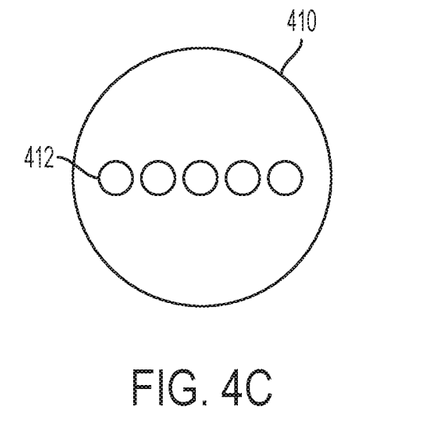
Figure 4D:
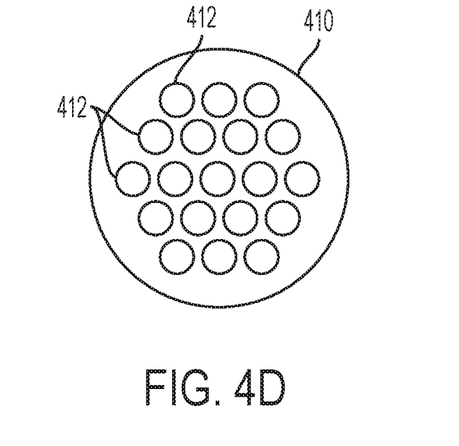

FIGS. 4C-4D are diagrams showing example layouts of the cores 412 in the optical fiber 410 of the photodisruption system 400. In the example shown in FIG. 4C, the cores 412 are arranged in one dimension across the cross-section of the optical fiber 410. In the example shown in FIG. 4D, the cores 412 are arranged in two dimensions across the cross-section of the optical fiber 410. The cores 412 may be arranged in another manner.

Figure 5:
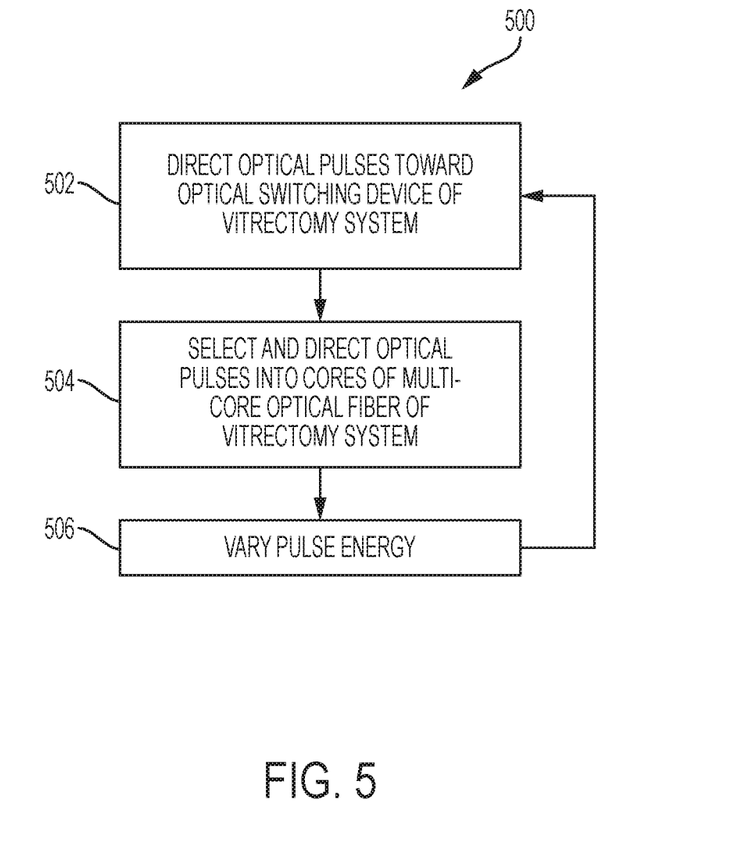
FIG. 5 is a flow diagram showing an example process for operating a photodisruption-based vitrectomy system.

FIG. 5 is a flow diagram showing an example process 500 for operating a photodisruption-based vitrectomy system. The process 500 may be implemented using the photodisruption-based vitrectomy system 100 of FIG. 1, the photodisruption-based vitrectomy system 400 of FIG. 4, or another type of photodisruption-based vitrectomy system to cause photodisruption in tissue (e.g., vitreous humor of an eye).

At 502, optical pulses are directed toward an optical switching device of a vitrectomy device. The optical pulses may be generated by a laser source similar to the laser source 402 of FIG. 4A. The optical pulses generated by the laser source may have an energy greater than a threshold energy for causing photodisruption in vitreous humor. For example, in some implementations, the optical pulses are generated by a femtosecond laser oscillator and have a pulse energy between 1 microjoule (µJ) to 10 millijoules (mJ), and a temporal width between 10-1000 femtoseconds (fs). The optical switching device may be implemented similar to the optical switching device 404 of FIG. 4A. For example, in some implementations, the optical switching device includes a microelectromechanical system (MEMS) device or a mirror galvanometer.

At 504, the optical switching device selects cores of a multi-core optical fiber in the vitrectomy device, and directs the optical pulse into the selected cores of the optical fiber. The optical fiber may be a glass core optical fiber with multiple cores, a hollow-core optical fiber with multiple cores, or another type of optical fiber with multiple cores. The cores of the optical fiber may be arranged in one or two dimensions within the optical fiber. The optical fiber may have a rounded tip that acts as a lens. The optical fiber may be arranged in a needle of a vitrectomy system such that the end of the optical fiber is situated proximate to an opening in the needle (e.g., as shown in FIG. 3 and described above). The optical switching device may selectively direct optical pulses into some or all of the cores of the optical fiber. For example, the optical switching device may selectively direct the optical pulses sequentially into each core of the multi-core fiber (e.g., in a raster-scan manner) or in another manner. The optical switching device may scan the cores of the optical fiber at a rate equal to the pulse rate of the laser source, or at another rate.

At 506, the pulse energy is varied by the laser source. The pulse energy may be increased or decreased from the pulse energy of the pulses at 502. For example, referring to FIG. 4B, the pulse energy may be increased in order to change the distance from the optical fiber at which photodisruption occurs, as described above. Once the energy is varied, the process 500 returns to 502, where the optical pulses with different pulse energy are directed toward the optical switching device. The optical pulses with the different pulse energy are then selectively directed into cores of the optical fiber at 504.

In some instances, the process 500 may allow for a first scan of each core of the optical fiber with optical pulses having a first energy, and then a second scan of each core with optical pulses having a second, increased energy. For example, a first area at a first depth from the optical fiber may be scanned to cause photodisruption, and then a second area at a second depth from the optical fiber may be scanned. In some instances, the process 500 may allow for a scan of depths in a first core, a scan of depths in a second core, and so on for each core of the optical fiber.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable subcombination.

A number of embodiments have been described. Nevertheless, it will be understood that various modifications can be made. Accordingly, other embodiments are within the scope of the following claims.

What is claimed is:

1. A photodisruption-based vitrectomy system comprising:
    a laser source configured to generate optical pulses having a pulse energy greater than a threshold energy for causing photodisruption in vitreous humor;
    an optical switching device arranged to receive an output of the laser source; and
    an optical fiber comprising multiple cores arranged in a pattern across a cross-sectional area of the optical fiber to define an area over which the photodisruption of the vitreous humor occurs at a distal end of the optical fiber disposed proximate an opening sized to allow the vitreous humor to enter the opening, the optical fiber arranged to receive an output of the optical switching device;
    wherein the optical switching device is configured to select a core of the optical fiber and direct optical pulses received from the laser source into the selected core;
    wherein the optical switching device is configured to scan the cores of the optical fiber to cover the defined area over which the photodisruption of the vitreous humor occurs at the distal end of the optical fiber.

2. The device of claim 1, wherein the optical switching device includes a microelectromechanical system (MEMS) device or a mirror galvanometer.

3. The device of claim 1, wherein the optical fiber is a hollow-core optical fiber.

4. The device of claim 1, wherein the pattern of the cores of the optical fiber is one dimensional.

5. The device of claim 1, wherein the pattern of the cores of the optical fiber is two dimensional.

6. The device of claim 1, comprising a lens disposed in an optical path between the optical switching device and the optical fiber.

7. The device of claim 1, wherein the laser source is configured to vary the pulse energy of the optical pulses to vary a distance from a proximal tip of the optical fiber at which photodisruption occurs.

8. A method for operating a photodisruption-based vitrectomy system comprising:
    directing an optical pulse generated by a laser source toward an optical switching device; and
    selecting, by the optical switching device, a core of an optical fiber, the optical fiber comprising multiple cores arranged in a pattern across a cross-sectional area of the optical fiber to define an area over which photodisruption of vitreous occurs at a distal end of the optical fiber disposed proximate an opening sized to allow the vitreous to enter the opening; and
    directing, by the optical switching device, the optical pulse into the selected core of the optical fiber;
    wherein the optical switching device is configured to scan the cores of the optical fiber to cover the defined area over which the photodisruption of the vitreous occurs at the distal end of the optical fiber;
    wherein the optical pulses have a pulse energy greater than a threshold energy for causing photodisruption in the vitreous humor.

9. The method of claim 7, comprising varying the pulse energy of the optical pulses generated by the laser source.

10. The method of claim 9, wherein the pulse energy of the optical pulses is increased after an optical pulse has been directed into each of the multiple cores of the optical fiber.

11. The method of claim 7, wherein directing the optical pulses into the selected core of the optical fiber comprises directing the optical pulses sequentially into each respective core of the optical fiber.

12. The method of claim 7, wherein the optical pulses have a pulse energy between 1 microjoule ($\mu J$) to 10 millijoules (mJ).

13. The method of claim 7, wherein the optical pulses have a temporal width between 10-1000 femtoseconds (fs).

14. An ophthalmic surgical system comprising:
    a console comprising:
        a laser source configured to generate optical pulses having a pulse energy greater than a threshold energy for causing photodisruption in vitreous humor;
        an optical switching device in optical communication with the laser source; and
    a handpiece coupled to the console, the handpiece comprising:
        a body;
        a needle extending from the body, the needle defining an opening; and
        an optical fiber disposed within the needle, the optical fiber comprising multiple cores, an end of the optical fiber disposed proximate to the opening in the needle, wherein the multiple cores are arranged in a pattern across a cross-sectional area of the optical fiber to define an area over which the photodisruption of the vitreous humor occurs at the end of the optical fiber disposed proximate the opening in the needle sized to allow the vitreous humor to enter the opening;
    wherein the optical switching device is configured to select a core of the optical fiber and direct optical pulses from the laser source into the selected core;
    wherein the optical switching device is configured to scan the cores of the optical fiber to cover the defined area over which the photodisruption of the vitreous humor occurs at the end of the optical fiber.

15. The system of claim 13, wherein the laser source is configured to generate pulses having a pulse energy between 1 microjoule ($\mu J$) to 10 millijoules (mJ), and a temporal width between 10-1000 femtoseconds (fs).

16. The system of claim 13, wherein the optical switching device includes a microelectromechanical system (MEMS) device or a mirror galvanometer.

17. The system of claim 13, wherein the optical fiber is a hollow-core optical fiber.

18. The system of claim 13, wherein the console comprises a vacuum source, the needle defines an aspiration lumen sized to allow fluid flow between the opening of the needle and the console, and the vacuum source is in fluid communication with the aspiration lumen.

19. The device of claim 13, the handpiece comprising a cannula disposed within the needle, wherein the optical fiber is disposed within the cannula.

20. The device of claim 13, wherein the laser source is configured to vary the pulse energy of the optical pulses.

\* \* \* \* \*